United States Patent
Seitz et al.

[11] Patent Number: 6,054,476
[45] Date of Patent: Apr. 25, 2000

[54] IMINOACETIC ACID AMIDES AND THEIR USE AS PEST CONTROL AGENTS

[75] Inventors: Thomas Seitz, Langenfeld; Klaus Stenzel, Düsseldorf, both of Germany

[73] Assignee: Bayer Aktiengesellschaft, Leverkusen, Germany

[21] Appl. No.: 09/051,593

[22] PCT Filed: Oct. 7, 1996

[86] PCT No.: PCT/EP96/04345

§ 371 Date: Apr. 15, 1998

§ 102(e) Date: Apr. 15, 1998

[87] PCT Pub. No.: WO97/14673

PCT Pub. Date: Apr. 24, 1997

[30] Foreign Application Priority Data

Oct. 18, 1995 [DE] Germany .............. 195 38 789

[51] Int. Cl.⁷ .............. A61K 31/38; A61K 31/16; C07D 333/56; C07D 307/02; A01N 43/10

[52] U.S. Cl. .............. 514/438; 514/443; 514/469; 514/471; 514/467; 514/619; 514/599; 549/58; 549/77; 549/430; 549/496; 549/467; 564/74; 564/168; 504/288; 504/336

[58] Field of Search .............. 564/74, 168; 562/621, 562/624; 549/430, 77, 58, 467, 496; 514/438, 443, 471, 469, 467, 599, 619; 504/288, 336

[56] References Cited

U.S. PATENT DOCUMENTS

| | | | |
|---|---|---|---|
| 5,194,662 | 3/1993 | Brand et al. | 560/35 |
| 5,221,691 | 6/1993 | Clough et al. | 514/619 |
| 5,393,782 | 2/1995 | Wingert et al. | 514/599 |
| 5,401,877 | 3/1995 | Hayase et al. | 564/167 |
| 5,763,640 | 6/1998 | De Fraine et al. | 560/35 |
| 5,889,059 | 3/1999 | Bayer et al. | 514/619 |

FOREIGN PATENT DOCUMENTS

602514 6/1994 European Pat. Off. .

OTHER PUBLICATIONS

Chemical Abstracts, vol. 65, No. 1, Jul. 4, 1966, Atsuo Kanai: "Studies on asymmertric . . . acid", XP002023285 & Nippon Kagaku Zasshi, vol. 87, No. 2, 1966, p. 18.

Indian Journal of chemistry, vol. 21B, 1982, pp. 348–351, XP000614358, A.S. Hammam et al.: "Synthesis and biological . . . carbazoquinones", pp. 348–349; examples IIID, E,F.

*Primary Examiner*—Deborah C. Lambkin
*Attorney, Agent, or Firm*—Norris, McLaughlin & Marcus, P.A.

[57] ABSTRACT

Iminoacetamides of the formula (I)

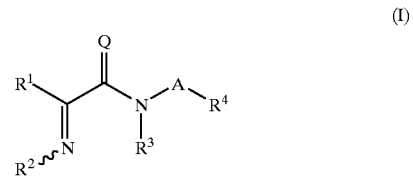

in which

A represents a single bond or optionally substituted alkylene,

Q represents oxygen or sulphur, $R^1$ represents respectively optionally substituted cycloalkyl, cycloalkenyl, aryl or heterocyclyl, $R^2$ represents respectively optionally substituted alkyl, alkenyl, alkinyl, cycloalkyl, cycloalkenyl, aryl or heterocyclyl, $R^3$ represents hydrogen or respectively optionally substituted alkyl, alkenyl, alkinyl or cycloalkyl, $R^4$ represents respectively optionally substituted cycloalkyl, cycloalkenyl, aryl or heterocyclcyl a process for their preparation, pesticidal compositions containing them, and their use for controlling pests.

10 Claims, No Drawings

IMINOACETIC ACID AMIDES AND THEIR USE AS PEST CONTROL AGENTS

This appln is a 371 of PCT/EP96/04345 Oct. 7, 1996.

The invention relates to novel iminoacetamides, to a process for their preparation and to their use as pesticides.

Novel compounds of the general formula (I) have been found

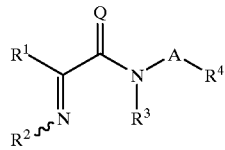

(I)

in which
- A represents a single bond or optionally substituted alkylene, Q represents oxygen or sulphur,
- $R^1$ represents respectively optionally substituted cycloalkyl, cycloalkenyl, aryl or heterocyclyl,
- $R^2$ represents respectively optionally substituted alkyl, alkenyl, alkinyl, cycloalkyl, cycloalkenyl, aryl or heterocyclyl,
- $R^3$ represents hydrogen or respectively optionally substituted alkyl, alkenyl, alkinyl or cycloalkyl,
- $R^4$ represents respectively optionally substituted cycloalkyl, cycloalkenyl, aryl or heterocylcyl.

In the definitions, the saturated or unsaturated hydrocarbon chains, such as alkyl, alkanediyl, alkenyl or alkinyl, including when combined with hetero atoms, as in alkoxy, alkylthio or alkylamino, are in each case straight-chain or branched.

Halogen generally represents fluorine, chlorine, bromine or iodine, preferably fluorine, chlorine or bromine, in particular fluorine or chlorine.

Aryl represents aromatic, mono or polycyclic hydrocarbon rings, such as, for example, phenyl, naphthyl, anthranyl, phenanthryl, preferably phenyl or naphthyl, in particular phenyl.

Heterocyclyl represents saturated or unsaturated and aromatic ring-shaped compounds in which at least one ring member is a hetero atom, i.e. an atom other than carbon. If the ring contains more than one hetero atom, these may be identical or different. Preferred hetero atoms are oxygen, nitrogen or sulphur.

Ring-shaped compounds optionally combine with further carbocyclic or heterocyclic, fused or bridged rings to form a polycyclic ring system. Preference is given to mono- or bicyclic ring systems, in particular to mono- or bicyclic aromatic ring systems.

Cycloalkyl represents saturated carbocyclic ring-shaped compounds which together with further carbocyclic, fused or bridged rings may form a polycyclic ring system.

Cycloalkenyl represents carbocyclic ring-shaped compounds which contain at least one double bond and which together with further carbocyclic, fused or bridged rings optionally form a polycyclic ring system.

Finally, it was found that the novel iminoacetamides of the general formula (I) have very strong fungicidal activity.

The compounds according to the invention may be present as mixtures of different possible isomeric forms, in particular of stereoisomers, such as, for example, E and Z, threo and erythro, and optical isomers. What is described and claimed includes both the E and the Z isomers, and also the threo and erythro and the optical isomers and any mixtures of these isomers.

The invention preferably provides compounds of the formula (I) in which
- A represents a single bond or represents alkylene having 1 to 6 carbon atoms which is optionally mono- or polysubstituted by identical or different substituents, the possible substituents preferably being selected from the list below:
  - halogen, cyano, nitro, amino, hydroxyl, formyl, carboxyl, carbamoyl, thiocarbamoyl;
  - respectively straight-chain or branched, alkoxy, alkylthio, alkylsulphinyl or alkylsulphonyl having in each case 1 to 6 carbon atoms;
  - respectively straight-chain or branched alkenyl or alkenyloxy having in each case 2 to 6 carbon atoms;
  - respectively straight-chain or branched, halogenoalkoxy, halogenoalkylthio, halogenoalkylsulphinyl or halogenoalkylsulphonyl having in each case 1 to 6 carbon atoms and 1 to 13 identical or different halogen atoms;
  - respectively straight-chain or branched halogenoalkenyl or halogenoalkenyloxy having in each case 2 to 6 carbon atoms and 1 to 13 identical or different halogen atoms;
  - respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties;
  - cycloalkyl having 3 to 6 carbon atoms;
  - and aryl or heterocyclyl, each of which is optionally mono- or polysubstituted by identical or different substituents from
  - halogen, cyano and/or straight-chain or branched alkyl having 1 to 4 carbon atoms
  - and/or straight-chain or branched halogenoalkyl having 1 to 4 carbon atoms and 1 to 9 identical or different halogen atoms
  - and/or straight-chain or branched alkoxy or alkylthio having 1 to 4 carbon atoms
  - and/or straight-chain or branched halogenoalkoxy or halogenoalkylthio having 1 to 4 carbon atoms and 1 to 9 identical or different halogen atoms
  - and/or respectively doubly attached alkylene or dioxyalkylene having in each case 1 to 6 carbon atoms, each of which is optionally mono- or polysubstituted by identical or different substituents from halogen and/or straight-chain or branched alkyl having 1 to 4 carbon atoms and/or straight-chain or branched halogenoalkyl having 1 to 4 carbon atoms and 1 to 9 identical or different halogen atoms.
- Q represents oxygen or sulphur,
- $R^1$ represents aryl, cycloalkyl or cycloalkenyl having 3 to 7 carbon atoms, or heterocyclyl having 3 to 12 ring members, each of which is optionally mono- or polysubstituted by identical or different substituents, the possible substituents preferably being selected from the list below:
  - halogen, cyano, nitro, amino, hydroxyl, formyl, carboxyl, carbamoyl, thiocarbamoyl;
  - respectively straight-chain or branched alkyl, alkoxy, alkylthio, alkylsulphinyl or alkylsulphonyl having in each case 1 to 8 carbon atoms;
  - respectively straight-chain or branched alkenyl or alkenyloxy having in each case 2 to 6 carbon atoms;
  - respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 8 carbon atoms in the individual alkyl moieties;

respectively doubly attached alkylene or dioxyalkylene having in each case 1 to 6 carbon atoms, each of which is optionally mono- or polysubstituted by halogen and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents from halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy or alkylthio having 1 to 4 carbon atoms and/or straight-chain or branched halogenoalkoxy or halogenoalkylthio having 1 to 4 carbon atoms and 1 to 9 identical or different halogen atoms and/or respectively doubly attached alkylene or dioxyalkylene having in each case 1 to 6 carbon atoms, each of which is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms.

$R^2$ represents alkyl having 1 to 4 carbon atoms, alkenyl or alkinyl having in each case 2 to 4 carbon atoms, each of which is optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which is optionally substituted by halogen) and optionally substituted phenyl, or represents aryl, cycloalkyl or cycloalkenyl having 3 to 7 carbon atoms, or heterocyclyl having 3 to 12 ring members, each of which is mono- or polysubstituted by identical or different substituents, the possible substituents preferably being selected from the list below:

halogen, cyano, nitro, amino, hydroxyl, formyl, carboxyl, carbamoyl, thiocarbamoyl;

respectively straight-chain or branched alkyl, alkoxy, alkylthio, alkylsulphinyl or alkylsulphonyl having in each case 1 to 8 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 8 carbon atoms in the individual alkyl moieties;

respectively doubly attached alkylene or dioxyalkylene having in each case 1 to 6 carbon atoms, each of which is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms, $R^3$ represents hydrogen or alkyl having 1 to 4 carbon atoms, $R^4$ represents aryl, cycloalkyl or cycloalkenyl having 3 to 8 carbon atoms, or heterocyclyl having 3 to 12 ring members, each of which is optionally mono- or polysubstituted by identical or different substituents, the possible substituents preferably being selected from the list below:

halogen, cyano, nitro, amino, hydroxyl, formyl, carboxyl, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties;

respectively doubly attached alkylene or dioxyalkylene having in each case 1 to 6 carbon atoms, each of which is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents from halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy or alkylthio having 1 to 4 carbon atoms and/or straight-chain or branched halogenoalkoxy or halogenoalkylthio having 1 to 4 carbon atoms and 1 to 9 identical or different halogen atoms and/or respectively doubly attached alkylene or dioxyalkylene having in each case 1 to 6 carbon atoms, each of which is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms.

The invention in particular provides compounds of the formula (I) in which

A represents a single bond or represents methylene, 1,1-ethylene, 1,2-ethylene 1,1-, 1,2-, 1,3- or 2,2-propylene, 1,1-, 1,2-, 1,3-, 1,4-, 2,2- or 2,3-butylene or 1,1-, 1,2- or 1,3-(2-methylpropylene), each of which is optionally mono- or polysubstituted by identical or different substituents from the group consisting of fluorine, chlorine, cyano and methoxy, Q represents oxygen or sulphur, $R^1$ represents respectively optionally mono- to trisubstituted cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl;

cyclopropyl, cyclobutyl, cyclopentyl or cyclohexyl;

phenyl, benzyl, phenoxy, benzyloxy, each of which is optionally substituted by the abovementioned substituents;

$R^2$ represents methyl, ethyl, n- or i-propyl, n-, i-, s- or t-butyl or propargyl or allyl or represents respectively optionally mono- to trisubstituted cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl;

or represents benzyl which is substituted the abovementioned substituents, $R^3$ represents hydrogen or represents methyl or ethyl, $R^4$ represents optionally mono- to trisubstituted cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl, cyclopropyl, cyclobutyl, cyclopentyl or cyclohexyl.

Particular preference is given to compounds of the formula (I) in which

A represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methylpropylene), each of which is optionally mono- or polysubstituted by identical or different substituents from the group consisting of fluorine, chlorine, cyano and methoxy, Q represents oxygen or sulphur, $R^1$ represents respectively optionally mono- to hexasubstituted cyclobutyl, cyclopentyl or cyclohexyl, preferred substituents being those listed below;

X represents respectively optionally mono- to trisubstituted phenyl, naphthyl, furyl, benzofuranyl, thienyl, benzothienyl, pyridyl, quinolyl, tetrahydrofuryl or perhydropyranyl, the possible substituents preferably being selected from the list below:

fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl; cyclopropyl, cyclopentyl, cyclohexyl; phenyl, phenoxy, benzyloxy, each of which is optionally substituted by the abovementioned substituents;

$R^2$ represents methyl, ethyl, n- or i-propyl, n-, i-, s- or t-butyl, allyl, or represents respectively optionally mono- to hexasubstituted cyclobutyl, cyclopentyl or cyclohexyl, preferred substituents being those listed below;

or represents respectively optionally mono- to trisubstituted phenyl, naphthyl, furyl, benzofuranyl, thienyl, benzothienyl, pyridyl, quinolyl, tetrahydrofuryl or perhydropyranyl, the possible substituents preferably being selected from the list below:

fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- or i-propyl, or represents benzyl which is substituted the abovementioned substituents, $R^3$ represents hydrogen or represents methyl, $R^4$ represents respectively optionally mono- to hexasubstituted cyclopropyl, cyclobutyl, cyclopentyl or cyclohexyl, preferred substituents being those listed below;

represents respectively optionally mono- to trisubstituted phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl;

cyclopropyl, cyclobutyl, cyclopentyl or cyclohexyl.

A very particularly preferred group of compounds according to the invention are those compounds of the formula (I) in which A represents a single bond or represents methylene, 1,1-ethylene, 1,2-ethylene, 1,1-propylene, 1,2-propylene, 1,3-propylene or 2,2-propylene, Q represents oxygen, $R^1$ represents phenyl, thienyl or furanyl, each of which is optionally mono- or disubstituted by bromine, chlorine, fluorine, nitro, methylsulphonyl, phenyl, phenyloxy, benzyloxy, cyclopropyl, cyclohexyl, methyl, ethyl, n- or i-propyl, n-, i-, s- or t-butyl, n-pentyl, n-hexyl, n-heptyl, methoxy, ethoxy, trifluoromethyl, trifluoromethoxy and/or methylthio, or represents phenyl which is substituted by 3,4-methylene- and ethylenedioxo, propane-1,3-diyl and butane-1,4-diyl, each of which is optionally substituted by fluorine, or represents naphthyl, benzofuranyl or benzothienyl, $R^2$ represents methyl or ethyl, represents n- or i-propyl, represents n-, i-, s- or t-butyl, allyl, cyclopentyl, cyclohexyl or represents optionally chlorine-, methyl- or methoxy-substituted phenyl or benzyl, $R^3$ represents hydrogen or methyl, $R^4$ represents cyclohexyl or optionally mono- to trisubstituted phenyl, thienyl, furyl, benzofuryl, benzothienyl, pyridyl, pyrimidinyl, naphthyl, quinolyl, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl, respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl.

Of very particular interest are compounds of the formula (I) in which the radical $R^1$ represents phenyl which is unsubstituted or substituted in position 3 and/or 4, or represents thienyl or furanyl which is unsubstituted or substituted in position 4 and/or 5, the substituents being selected from the abovementioned group, in particular chlorine, bromine, fluorine, nitro, methylsulphonyl, phenyl, phenoxy, benzyloxy, cyclopropyl, cyclohexyl, methyl, ethyl, n-, i-propyl, n-, i-, s-, t-butyl, n-pentyl, n-hexyl, n-heptyl, methoxy, ethoxy, methylthio, trifluoromethyl and trifluoromethoxy, or phenyl which is substituted by 3,4-methylene- and ethylenedioxo, propane-1,3-diyl and butane-1,4-diyl, each of which is optionally substituted by fluorine, or benzofuranyl, benzothienyl or naphthyl which is substituted in position 2.

Particular preference is also given to compounds of the formula (I) in which $R^4$ represents phenyl which is substituted by methoxy in positions 3 and 4.

The abovementioned general or preferred definitions of a radical apply both to the end products of the formula (I) and, correspondingly, to the starting materials or intermediates required in each case for the preparation.

These definitions of a radical can be combined with each other as desired, that is to say combinations between the ranges stated for preferred compounds are also possible.

Specific preferred compounds are listed in the tables below:

TABLE 1

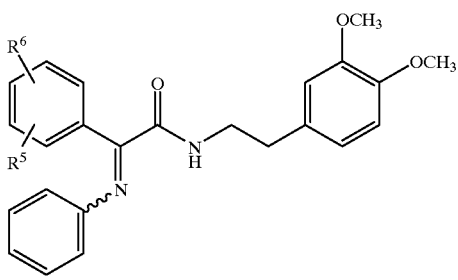

(Ia)

| Compound No. | $R^5$ | $R^6$ |
|---|---|---|
| Ia-1 | hydrogen | hydrogen |
| Ia-2 | 4-chloro | hydrogen |
| Ia-3 | 4-fluoro | hydrogen |
| Ia-4 | 4-bromo | hydrogen |
| Ia-5 | 4-methyl | hydrogen |
| Ia-6 | 4-ethyl | hydrogen |
| Ia-7 | 4-iso-propyl | hydrogen |
| Ia-8 | 4-n-propyl | hydrogen |
| Ia-9 | 4-n-butyl | hydrogen |
| Ia-10 | 4-iso-butyl | hydrogen |
| Ia-11 | 4-tert-butyl | hydrogen |
| Ia-12 | 4-sec-butyl | hydrogen |
| Ia-13 | 4-methoxy | hydrogen |
| Ia-14 | 4-ethoxy | hydrogen |
| Ia-15 | 4-methylthio | hydrogen |
| Ia-16 | 4-trifluoromethyl | hydrogen |
| Ia-17 | 3-chloro | hydrogen |
| Ia-18 | 3-fluoro | hydrogen |
| Ia-19 | 3-bromo | hydrogen |
| Ia-20 | 3-methyl | hydrogen |
| Ia-21 | 3-ethyl | hydrogen |
| Ia-22 | 3-iso-propyl | hydrogen |
| Ia-23 | 3-n-propyl | hydrogen |
| Ia-24 | 3-n-butyl | hydrogen |
| Ia-25 | 3-iso-butyl | hydrogen |
| Ia-26 | 3-tert-butyl | hydrogen |
| Ia-27 | 3-sec-butyl | hydrogen |
| Ia-28 | 3-methoxy | hydrogen |
| Ia-29 | 3-ethoxy | hydrogen |
| Ia-30 | 3-methylthio | hydrogen |
| Ia-31 | 3-trifluoromethyl | hydrogen |
| Ia-32 | 3,4-dichloro | hydrogen |
| Ia-33 | 3,4-difluoro | hydrogen |
| Ia-34 | 3,4-dibromo | hydrogen |
| Ia-35 | 3,4-dimethyl | hydrogen |
| Ia-36 | 3,4-diethyl | hydrogen |
| Ia-37 | —O—CH$_2$—O—* | |
| Ia-38 | —O—CN$_2$—CN$_2$—O—* | |
| Ia-39 | —O—CF$_2$—O—* | |
| Ia-40 | —O—CF$_2$—CF$_2$—O—* | |
| Ia-41 | —(CH$_2$)$_3$—* | |
| Ia-42 | —(CH$_2$)$_4$—* | |
| Ia-43 | 3-methoxy | 4-methoxy |
| Ia-44 | 3-ethoxy | 4-ethoxy |
| Ia-45 | 3-methylthio | 4-methylthio |
| Ia-46 | 3-trifluoromethyl | 4-trifluoromethyl |
| Ia-47 | 3-chloro | 4-methyl |
| Ia-48 | 4-chloro | 3-methyl |
| Ia-49 | 3-chloro | 4-methoxy |
| Ia-50 | 4-chloro | 3-methoxy |
| Ia-51 | 3-chloro | 4-ethyl |
| Ia-52 | 4-chloro | 3-ethyl |
| Ia-53 | 3-methoxy | 4-ethoxy |
| Ia-54 | 4-methoxy | 3-ethoxy |
| Ia-55 | 3-methyl | 4-methoxy |
| Ia-56 | 4-methyl | 3-methoxy |
| Ia-57 | 3-methyl | 4-ethyl |
| Ia-58 | 4-methyl | 3-ethyl |
| Ia-59 | 3-methoxy | 4-ethyl |
| Ia-60 | 4-methoxy | 3-ethyl |
| Ia-61 | 4-nitro | hydrogen |

TABLE 1-continued (Ia)

| Compound No. | R⁵ | R⁶ |
|---|---|---|
| Ia-62 | 4-methylsulphonyl | hydrogen |
| Ia-63 | 4-phenoxy | hydrogen |
| Ia-64 | 4-phenyl | hydrogen |
| Ia-65 | 4-benzyloxy | hydrogen |
| Ia-66 | 4-pentyl | hydrogen |
| Ia-67 | 4-hexyl | hydrogen |
| Ia-68 | 4-heptyl | hydrogen |
| Ia-69 | 4-cyclopropyl | hydrogen |
| Ia-70 | 4-cyclohexyl | hydrogen |

*In each case attached in positions 3 and 4

TABLE 2

(Ib)

| Compound No. | R⁵ | R⁶ |
|---|---|---|
| Ib-1 | hydrogen | hydrogen |
| Ib-2 | 4-chloro | hydrogen |
| Ib-3 | 4-fluoro | hydrogen |
| Ib-4 | 4-bromo | hydrogen |
| Ib-5 | 4-methyl | hydrogen |
| Ib-6 | 4-ethyl | hydrogen |
| Ib-7 | 4-iso-propyl | hydrogen |
| Ib-8 | 4-n-propyl | hydrogen |
| Ib-9 | 4-n-butyl | hydrogen |
| Ib-10 | 4-iso-butyl | hydrogen |
| Ib-11 | 4-tert-butyl | hydrogen |
| Ib-12 | 4-sec-butyl | hydrogen |
| Ib-13 | 4-methoxy | hydrogen |
| Ib-14 | 4-ethoxy | hydrogen |
| Ib-15 | 4-methylthio | hydrogen |
| Ib-16 | 4-trifluoromethyl | hydrogen |
| Ib-17 | 5-chloro | hydrogen |
| Ib-18 | 5-fluoro | hydrogen |
| Ib-19 | 5-bromo | hydrogen |
| Ib-20 | 5-methyl | hydrogen |
| Ib-21 | 5-ethyl | hydrogen |
| Ib-22 | 5-iso-propyl | hydrogen |
| Ib-23 | 5-n-propyl | hydrogen |
| Ib-24 | 5-n-butyl | hydrogen |
| Ib-25 | 5-iso-butyl | hydrogen |
| Ib-26 | 5-sec-butyl | hydrogen |
| Ib-27 | 5-tert-butyl | hydrogen |
| Ib-28 | 5-methoxy | hydrogen |

TABLE 2-continued (Ib)

| Compound No. | R⁵ | R⁶ |
|---|---|---|
| Ib-29 | 5-ethoxy | hydrogen |
| Ib-30 | 5-methylthio | hydrogen |
| Ib-31 | 5-trifluoromethyl | hydrogen |
| Ib-32 | 4-chloro | 5-chloro |
| Ib-33 | 4-fluoro | 5-fluoro |
| Ib-34 | 4-bromo | 5-bromo |
| Ib-35 | 4-methyl | 5-methyl |
| Ib-36 | 4-ethyl | 5-ethyl |
| Ib-37 | 4-methoxy | 5-methoxy |
| Ib-38 | 4-trifluoromethyl | 5-trifluoromethyl |
| Ib-39 | 4-chloro | 5-methyl |
| Ib-40 | 5-chloro | 4-methyl |

TABLE 3

(Ic)

| Compound No. | R⁵ | R⁶ |
|---|---|---|
| Ic-1 | hydrogen | hydrogen |
| Ic-2 | 4-chloro | hydrogen |
| Ic-3 | 4-fluoro | hydrogen |
| Ic-4 | 4-bromo | hydrogen |
| Ic-5 | 4-methyl | hydrogen |
| Ic-6 | 4-ethyl | hydrogen |
| Ic-7 | 4-iso-propyl | hydrogen |
| Ic-8 | 4-n-propyl | hydrogen |
| Ic-9 | 4-n-butyl | hydrogen |
| Ic-10 | 4-iso-butyl | hydrogen |
| Ic-11 | 4-tert-butyl | hydrogen |
| Ic-12 | 4-sec-butyl | hydrogen |
| Ic-13 | 4-methoxy | hydrogen |
| Ic-14 | 4-ethoxy | hydrogen |
| Ic-15 | 4-methylthio | hydrogen |
| Ic-16 | 4-trifluoromethyl | hydrogen |
| Ic-17 | 5-chloro | hydrogen |
| Ic-18 | 5-fluoro | hydrogen |
| Ic-19 | 5-bromo | hydrogen |
| Ic-20 | 5-methyl | hydrogen |
| Ic-21 | 5-ethyl | hydrogen |
| Ic-22 | 5-iso-propyl | hydrogen |
| Ic-23 | 5-n-propyl | hydrogen |
| Ic-24 | 5-n-butyl | hydrogen |
| Ic-25 | 5-iso-butyl | hydrogen |
| Ic-26 | 5-sec-butyl | hydrogen |
| Ic-27 | 5-tert-butyl | hydrogen |

TABLE 3-continued

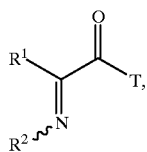
(Ic)

| Compound No. | R⁵ | R⁶ |
|---|---|---|
| Ic-28 | 5-methoxy | hydrogen |
| Ic-29 | 5-ethoxy | hydrogen |
| Ic-30 | 5-methylthio | hydrogen |
| Ic-31 | 5-trifluoromethyl | hydrogen |
| Ic-32 | 4-chloro | 5-chloro |
| Ic-33 | 4-fluoro | 5-fluoro |
| Ic-34 | 4-bromo | 5-bromo |
| Ic-35 | 4-methyl | 5-methyl |
| Ic-36 | 4-ethyl | 5-ethyl |
| Ic-37 | 4-methoxy | 5-methoxy |
| Ic-38 | 4-trifluoromethyl | 5-trifluoromethyl |
| Ic-39 | 4-chloro | 5-methyl |
| Ic-40 | 4-methyl | 4-methyl |

TABLE 4

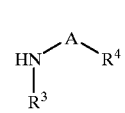
(Id)

| Compound No. | R¹ |
|---|---|
| Id-1 | 2-naphthyl |
| Id-2 | 2-benzofuranyl |
| Id-3 | 2-benzothienyl |

Table 5

Compounds Ia-1 to Id-3 corresponding to the formulae Ia, Ib, Ic and Id where the 3,4-dimethoxyphenyl group (generally denoted R⁴) has been replaced by one of the following trisubstituted phenyl radicals: substituents: 3,4,5-trimethoxy; 3,4,5-trichloro; 3,4,5-trimethyl.

Furthermore, it has been found that the novel iminoacetamides of the general formula (I) are obtained when carboxylic acid derivatives of the general formula (II)

$$\begin{array}{c}\text{(II)}\\ R^1\\ \diagdown\\ \diagup C-C\diagup\\ R^2\diagup N\end{array}\begin{array}{c}O\\ \|\\ \diagdown T,\end{array}$$

in which
R¹, R² and Q are each as defined above and
T represents hydroxyl, halogen or alkoxy,
are reacted with an amine of the general formula (III), $$HN(A)(R^3)R^4 \quad \text{(III)}$$

in which
R³, R⁴ and A are each as defined above
or with a hydrogen halide thereof
if appropriate in the presence of an acid acceptor, if appropriate in the presence of a condensing agent, if appropriate in the presence of a catalyst and if appropriate in the presence of a diluent.

Formula (II) provides a general definition of the carboxylic acid derivatives required as starting materials for carrying out the process according to the invention. In this formula (II), (Q, R¹ and R²) each preferably have in particular those meanings which have already been indicated in connection with the description of the compounds of the formula (I) according to the invention as preferred or as particularly preferred for (Q, R¹ and R²); T preferably represents alkoxy having 1 to 4 carbon atoms, in particular represents methoxy or ethoxy, represents hydroxyl or chlorine.

The starting materials of the formula (II) are known and/or can be prepared by known processes (cf. for example, Tetrahedron 1971, 3431–6).

Formula (III) provides a general definition of the amines further to be used as starting materials. In this formula (II), R³, R⁴ and A each preferably have in particular those meanings which have already been indicated in connection with the description of the compounds of the formula (I) according to the invention as preferred or as particularly preferred for R³, R⁴ and A.

The starting materials of the formula (III) are known organic chemicals for synthesis and/or can be prepared by methods known per se.

If appropriate, the process according to the invention is carried out in the presence of a suitable acid acceptor. Suitable as acid acceptors are all conventional inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylanilin, N,N-dimethylbenzylamine, pyridine, N-methylpiperidine, N,N-dimethylaminopyridine, diazabicyclooctane (DABCO), diazabicyclononene (DBN) or diazabicycloundecene (DBU).

If appropriate, the process according to the invention is carried out in the presence of a suitable condensing agent. Suitable condensing agents are all condensing agents which are conventionally used for such amidation reactions. Examples include acid halide formers such as phosgene, phosphorus tribromide, phosphorus trichloride, phosphorus pentachloride, phosphorus oxychloride or thionyl chloride; anhydride formers such as ethyl chloroformate, methyl chloroformate or methanesulphonyl chloride; carbodiimides, such as N,N'-dicyclohexylcarbodiimide (DCC), or other conventional condensing agents, such as phosphorus pentoxide, polyphosphoric acid, N,N'-carbonyldiimidazole, 2-ethoxy-N-ethoxycarbonyl- 1,2-dihydroquinoline (EEDQ) or triphenylphosphine/carbon tetrachloride.

If appropriate, the process according to the invention is carried out in the presence of a diluent. Suitable diluents for carrying out the process according to the invention are water and organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxan, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol, ethylene glycol monomethyl ether, ethylene glycol monoethyl ether, diethylene glycol monomethyl ether, diethylene glycol monoethyl ether, their mixtures with water or pure water.

If appropriate, the process according to the invention is carried out in the presence of a catalyst. Examples include 4-dimethylaminopyridine, 1-hydroxy-benzotriazole and dimethylformamide.

When carrying out the process according to the invention, the reaction temperatures may be varied within a relatively wide range. In general, temperatures between −20° C. and +200° C., preferably temperatures between 0° C. and 150° C., are employed.

In the practice of the process according to the invention, generally 1 to 5 mol, preferably 1.0 to 2.5 mol, of amine are employed per mole of carboxylic acid derivative of the formula (II).

The reaction is carried out and reaction products are worked up and isolated according to known processes (cf. the Preparation Example).

The process according to the invention may also be carried out as a two-step process. For this purpose, the carboxylic acid derivatives of the general formula (II) are initially converted into an activated form and reacted with the amines of the general formula (III) in a subsequent step to give the iminoacetamides of the general formula (I) according to the invention.

Suitable activated forms of the carboxylic acid derivatives of the formula (II) are all carboxy-activated derivatives, such as, for example, acyl halides, preferably acyl chlorides, acyl azides, further symmetric and mixed anhydrides, such as, for example, the mixed O-alkylcarbonic anhydrides, furthermore activated esters, such as, for example, p-nitrophenyl esters or N-hydroxysuccinimide esters and adducts with condensing agents, such as, for example, dicyclohexylcarbodiimide or activated forms of the carboxylic acids prepared in situ.

The active compounds according to the invention have potent microbicidal activity and may be employed in practice for controlling undesirable microorganisms. The active compounds are suitable for use as crop protection agents, in particular as fungicides.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora*;

Pythium species, such as, for example, *Pythium ultimum*;

Phytophthora species, such as, for example, *Phytophthora infestans*;

Pseudoperonospora species, such as, for example, *Pseudoperonospora humuli* or *Pseudoperonospora cubensis*;

Plasmopara species, such as, for example, *Plasmopara viticola*;

Bremia species, such as, for example, *Bremia lactucae*;

Peronospora species, such as, for example, *Peronospora pisi* or *Peronospora brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis*;

Pyrenophora species, such as, for example, *Pyrenophora teres* or *Pyrenophora graminea*

(conidial form: Drechslera, synonym: Helminthosporium);

Cochliobolus species, such as, for example, *Cochliobolus sativus*

(conidial form: Drechslera, synonym: Helminthosporium);

Uromyces species, such as, for example, *Uromyces appendiculatus*;

Puccinia species, such as, for example, *Puccinia recondita*;

Sclerotinia species, such as, for example, *Sclerotinia sclerotiorum*;

Tilletia species, such as, for example, *Tilletia caries*;

Ustilago species, such as, for example, *Ustilago nuda* or *Ustilago avenae*;

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The fact that the active compounds are well tolerated by plants at the concentrations required for-controlling plant diseases permits the treatment of aerial parts of plants, of propagation stock and seeds, and of the soil.

The active compounds according to the invention can be employed particularly successfully for controlling diseases in viticulture, fruit-growing and vegetable-growing, for example against Plasmopara species and Phytophthora species. They can also be employed very successfully for controlling rice diseases, for example Pyricularia species.

Depending on their particular physical and/or chemical properties, the active compounds are converted into the customary formulations, such as solutions, emulsions, suspensions, powders, foams, pastes, granules, aerosols and microencapsulations in polymeric substances and in coating compositions for seeds, and ULV cold and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. Essentially, the following are suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water; liquefied gaseous extenders or carriers are to be understood as meaning liquids which are gaseous at ambient temperature and under atmospheric pressure, for example aerosol propellants such as halogenated hydrocarbons, or else butane, propane, nitrogen and carbon dioxide; suitable solid carriers are: for example, ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example, crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or, in their formulations, also as a mixture with known fungicides, bactericides, acaricides, nematicides or insecticides in order thus, for example, to widen the spectrum of action or to prevent development of resistance. In many cases, synergistic effects are achieved, i.e. the activity of the mixture is greater than the activity of the individual components.

In many cases synergistic effects are observed.

Particularly advantageous examples of co-components for mixtures are the following compounds:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxy-phenyl)-acetamide; 8-hydroxyquinoline sulphate; methyl (E)-2-{2-[6-(2-cyanophenoxy)-pyrimidin-4-yloxy]phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thio-phanate-methyl, thiram, tolclophos-methyl, tolylfluanid, triadimefon, triadimenol, triazoxide, trichlamide, tricyclazole, tridemorph, triflumizole, triforine, triticonazole,
validamycin A, vinclozolin,
zineb, ziram.
Bactericides
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.
Insecticides/Acaricides/Nematicides
abamectin, abamectin, acephate, acrinathrin, alanycarb, aldicarb, alphamethrin, amitraz, avermectin, AZ 60541, azadirachtin, azinphos A, azinphos M, azocyclotin,
*Bacillus thuringiensis*, 4-bromo-2-(4-chlorophenyl)-1-(ethoxymethyl)-5-(trifluoromethyl)-1H-pyrrole-3-carbonitrile, bendiocarb, benfuracarb, bensultap, betacyluthrin, bifenthrin, BPMC, brofenprox, bromophos A, bufencarb, buprofezin, butocarboxin, butylpyridaben,
cadusafos, carbaryl, carbofuran, carbophenothion, carbosulfan, cartap, chloethocarb, chlorethoxyfos, chloretoxyfos, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophos, etofenprox, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivemectin,
lamda-cyhalothrin, lufenuron,
malathion, mecarbam, mervinphos, mesulfenfos, metaldehyde, methacrifos, methamidophos, methidathion, methiocarb, methomyl, metolcarb, milbemectin, monocrotophos, moxidectin,
naled, NC 184, nitenpyram
omethoate, oxamyl, oxydemethon M, oxydeprofos,
parathion A, parathion M, permethrin, phenthoate, phorate, phosalone, phosmet, phosphamdon, phoxim, pirimicarb, pirimiphos M, primiphos A, profenofos, profenophos, promecarb, propaphos, propoxur, prothiofos, prothiophos, prothoate, pymetrozin, pyrachlophos, pyraclofos, pyraclophos, pyradaphenthion, pyresmethrin, pyrethrum, pyridaben, pyrimidifen, pyriproxifen,
quinalphos,
salithion, sebufos, silafluofen, sulfotep, sulprofos,
tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb,
vamidothion, XMC, xylylcarb, YI 5301/5302, zetamethrin.

A mixture with other known active compounds, such as herbicides, or fertilizers and growth regulators, is also possible.

The active compounds according to the invention can be used as such or in the form of their commercially available formulations or the use forms prepared therefrom, such as ready-to-use solutions, suspensions, wettable powders, pastes, soluble powders, dusts and granules. They are used in the customary manner, for example by watering, spraying, atomizing, scattering, foaming, brushing on and the like. If appropriate, the active compounds are applied by the ultra-low volume method, or the active compound formulation, or the active compound itself, are injected into the soil. The seeds of the plants can also be treated, if appropriate.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seeds.

In the treatment of the soil, active compound concentrations of from 0.00001 to 0.1% by weight, preferably from 0.0001 to 0.02% by weight, are required at the treatment site.

PREPARATION EXAMPLES

Example 1

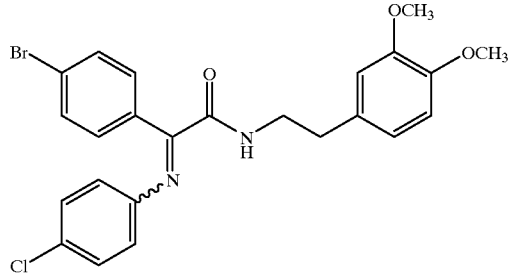

5.5 g (0.015 mol) of ethyl 2-(4-chlorophenylimino)-2-(4-bromophenyl)-acetate, 2.72 g (0.015 mol) of 2-(3,4-dimethoxyphenyl)-ethylamine and 5.4 g (0.03 mol) of 30% strength methanolic sodium methoxide solution in 30 ml of methanol are heated to boiling for 18 hours. The solvent is distilled off and the residue is taken up in dichloromethane and washed successively with 1 N hydrochloric acid and water, and the organic phase is dried over sodium sulphate. The solvent is distilled off under reduced pressure and the residue is chromatographed over silica gel using petroleum ether/ethyl acetate (3:1). 2.5 g (33% of theory) of a mixture of e and z-N-[2-(3,4-dimethoxyphenyl)-ethyl]-2-(4-chlorophenylimino)-2-(4-bromophenyl)-acetamide are obtained as an oil.

$^1$H NMR (CDCl$_3$, TMS): δ (ppm)=3.87 (s, 3H).

By a method similar to Example 1, and according to the procedures of the general description of the process, the compounds of the formula (Ie) mentioned in Table 6 below are obtained.

TABLE 6
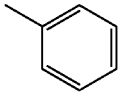
(Ie)
| Ex. No. | R⁵ | R⁶ | R² | E/Z | physical data |
|---|---|---|---|---|---|
| 2 | 4-C₂H₅ | H | CH(CH₃)₂ | E/Z | *)1H NMR: 1.10 (d,3H) |
| 3 | 4-C₂H₅ | H | 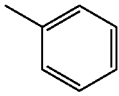 | E/Z | *)1H NMR: 3.87 (s,3H) |
| 4 | 4-Cl | H | 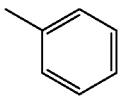 | Z | log P: 4.32 |
| 5 | 4-CH₃ | H | 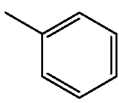 | Z | *)1H NMR: 3.87 (s,3) |
| 6 | —(CH₂)₄—** | | 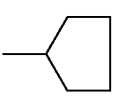 | Z | *)1H NMR: 3.87 (s,3H) |
| 7 | 4-Cl | H | 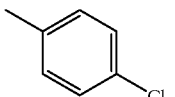 | E/Z | *)1H NMR: 3.87 (s,3H) |
| 8 | 4-Cl | H | 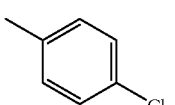 | E/Z | *)1H NMR: 3.88 (s,3H) |
| 9 | 4-C₂H₅ | H | 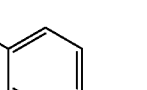 | E/Z | mp.: 71–72° C. |
| 10 | 4-C₂H₅ | H | 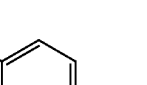 | E/Z | *)1H NMR: 3.87 (s,3H) |
| 11 | 4-C₂H₅ | H | 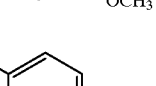 | E/Z | *)1H NMR: 3.73 (s,3H) |
| 12 | 4-Br | H |  | E/Z | *)1H NMR: 3.87 (s,3H) |

TABLE 6-continued
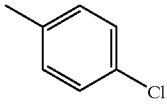
(Ie)
| Ex. No. | R⁵ | R⁶ | R² | E/Z | physical data |
|---|---|---|---|---|---|
| 13 | —(CH₂)₃—** | H | 4-Cl-C₆H₄- | Z | *)1H NMR: 3.88 (s,3H) |
| 14 | —(CH₂)₄— | ** | 4-Cl-C₆H₄- | E/Z | *)1H NMR: 3.86 (s,3H) |
| 15 | 4-CH₃ | H | 4-Cl-C₆H₄- | E/Z | *)1H NMR: 3.86 (s,3H) |
| 16 | 4-Br | H | C₆H₅- | E/Z | *)1H NMR: 3.87 (s,3H) |
| 17 | 4-Br | H | 4-OCH₃-C₆H₄- | E/Z | *)1H NMR: 3.88 (s,3H) |
| 18 | —(CH₂)₃—** | | 4-OCH₃-C₆H₄- | E/Z | *)1H NMR: 3.75 (s,3H) |
| 19 | —(CH₂)₃—** | | 4-CH₃-C₆H₄- | E/Z | *)1H NMR: 3.86 (s,3H) |
| 20 | —(CH₂)₄—** | | 4-CH₃-C₆H₄- | E/Z | *)1H NMR: 3.88 (s,3H) |
| 21 | 4-Br | H | cyclopentyl | E/Z | *)1H NMR: 3.88 (s,3H) |
| 22 | 4-CH₃ | H | 4-OCH₃-C₆H₄- | E/Z | mp.: 73–74° C. |

TABLE 6-continued

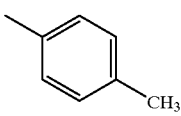

(Ie)

| Ex. No. | R⁵ | R⁶ | R² | E/Z | physical data |
|---|---|---|---|---|---|
| 23 | 4-CH₃ | H | 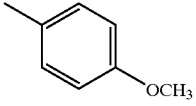 | E/Z | *)1H NMR: 2.19 (s,3H) |
| 24 | 4-Cl | H | 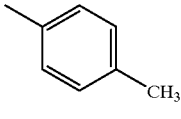 | E/Z | mp.: 137° C. |
| 25 | 4-Cl | H | 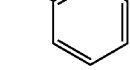 | E/Z | mp.: 122° C. |
| 26 | —(CH₂)₃—** | | 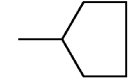 | E/Z | *)1H NMR: 3.87 (s,3H) |
| 27 | —(CH₂)₃—** | | 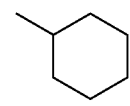 | E/Z | *)1H NMR: 3.88 (s,3H) |
| 28 | —(CH₂)₃—** | | 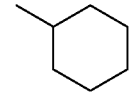 | E/Z | *)1H NMR: 3.87 (s,3H) |
| 29 | 4-Br | H | 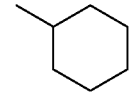 | E/Z | *)1H NMR: 3.89 (s,3H) |

*)The 1H NMR spectra were recorded in deuterochloroform (CDCl₃) or hexadeuterodimethyl sulphoxide (DMSO-d₆) using tetramethylsilane (TMS) as internal standard. The chemical shift is given as d value in ppm.
**)In each case attached in positions 3 and 4.

Use Examples

Example A

Phytophthora test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous suspension of spores of Phytophthora infestans.

The plants are placed in an incubation cabinet at a relative atmospheric humidity of 100% and approximately 20° C.

Evaluation is carried out 3 days after the inoculation.

In this test, for example the following compounds (1), (6), (7), (16), (17), (18) and (24) of the preparation examples exhibit, at an active compound concentration of 50 ppm, an efficacy of up to 98%.

We claim:
1. Compounds of the general formula (I)

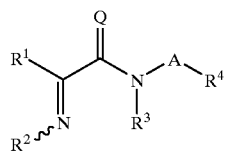

(I)

in which
A represents a single bond or optionally substituted alkylene,
Q represents oxygen or sulphur,
$R^1$ represents respectively optionally substituted cycloalkyl, cycloalkenyl, aryl or heterocyclyl,
$R^2$ represents respectively optionally substituted alkyl, alkenyl, alkinyl, cycloalkyl, cycloalkenyl, aryl or heterocyclyl,
$R^3$ represents hydrogen or respectively optionally substituted alkyl, alkenyl, alkinyl or cycloalkyl,
$R^4$ represents respectively optionally substituted cycloalkyl, cycloalkenyl, aryl or heterocyclcyl.

2. Compounds of the formula (I) according to claim 1, in which
A represents a single bond or represents alkylene having 1 to 6 carbon atoms which is optionally mono- or polysubstituted by identical or different substituents, the substituents being selected from the group consisting of:
halogen, cyano, nitro, amino, hydroxyl, formyl, carboxy, carbamoyl, thiocarbamoyl;
respectively straight-chain or branched, alkoxy, alkylthio, alkylsulphinyl or alkylsulphonyl having in each case 1 to 6 carbon atoms;
respectively straight-chain or branched alkenyl or alkenyloxy having in each case 2 to 6 carbon atoms;
respectively straight-chain or branched, halogenoalkoxy, halogenoalkylthio, halogenoalkylsulphinyl or halogenoalkylsulphonyl having in each case 1 to 6 carbon atoms and 1 to 13 identical or different halogen atoms;
respectively straight-chain or branched halogenoalkenyl or halogenoalkenyloxy having in each case 2 to 6 carbon atoms and 1 to 13 identical or different halogen atoms;
respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties;
cycloalkyl having 3 to 6 carbon atoms;
and aryl or heterocyclyl, each of which is optionally mono- or polysubstituted by identical or different substituents selected from the group consisting of:
halogen, cyano and/or straight-chain or branched alkyl having 1 to 4 carbon atoms;
and/or straight-chain or branched halogenoalkyl having 1 to 4 carbon atoms and 1 to 9 identical or different halogen atoms;
and/or straight-chain or branched alkoxy or alkylthio having 1 to 4 carbon atoms;
and/or straight-chain or branched halogenoalkoxy or halogenoalkylthio having 1 to 4 carbon atoms and 1 to 9 identical or different halogen atoms;
and/or respectively doubly attached alkylene or dioxyalkylene having in each case 1 to 6 carbon atoms, each of which is optionally mono- or polysubstituted by identical or different substituents from halogen and/or straight-chain or branched alkyl having 1 to 4 carbon atoms and/or straight-chain or branched halogenoalkyl having 1 to 4 carbon atoms and 1 to 9 identical or different halogen atoms;
Q represents oxygen or sulphur,
$R^1$ represents aryl, cycloalkyl or cycloalkenyl having 3 to 7 carbon atoms, or heterocyclyl having 3 to 12 ring members, each of which is optionally mono- or polysubstituted by identical or different substituents, the substituents being selected from the group consisting of:
halogen, cyano, nitro, amino, hydroxyl, formyl, carboxy, carbamoyl, thiocarbamoyl;
respectively straight-chain or branched alkyl, alkoxy, alkylthio, alkylsulphinyl or alkylsulphonyl having in each case 1 to 8 carbon atoms;
respectively straight-chain or branched alkenyl or alkenyloxy having in each case 2 to 6 carbon atoms;
respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
respectively straight-chain or branched halogenoalkenyl or halogenoalkenyloxy having in each case 2 to 6 carbon atoms and 1 to 13 identical or different halogen atoms;
respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 8 carbon atoms in the individual alkyl moieties;
respectively doubly attached alkylene or dioxyalkylene having in each case 1 to 6 carbon atoms, each of which is optionally mono- or polysubstituted by halogen and/or straight-chain or branched alkyl having 1 to 4 carbon atoms and/or straight-chain or branched halogenoalkyl having 1 to 4 carbon atoms and 1 to 9 identical or different halogen atoms;
cycloalkyl having 3 to 6 carbon atoms;
and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio,
each of which is optionally mono- or polysubstituted by identical or different substituents selected from the group consisting of:
halogen, cyano and/or straight-chain or branched alkyl having 1 to 4 carbon atoms;
and/or straight-chain or branched halogenoalkyl having 1 to 4 carbon atoms and 1 to 9 identical or different halogen atoms;
and/or straight-chain or branched alkoxy or alkylthio having 1 to 4 carbon atoms;
and/or straight-chain or branched halogenoalkoxy or halogenoalkylthio having 1 to 4 carbon atoms and 1 to 9 identical or different halogen atoms;
and/or respectively doubly attached alkylene or dioxyalkylene having in each case 1 to 6 carbon atoms, each of which is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms;

$R^2$ represents alkyl having 1 to 4 carbon atoms, alkenyl or alkinyl having in each case 2 to 4 carbon atoms, each of which is optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and Cl-$C_4$-alkylsulphonyl (each of which is optionally substituted by halogen) and optionally substituted phenyl, or represents aryl, cycloalkyl or cycloalkenyl having 3 to 7 carbon atoms, or heterocyclyl having 3 to 12 ring members, each of which is mono- or polysubstituted by identical or different substituents, the substituents being selected from the group consisting of:

halogen, cyano, nitro, amino, hydroxyl, formyl, carboxy, carbamoyl, thiocarbamoyl;

respectively straight-chain or branched alkyl, alkoxy, alkylthio, alkylsulphinyl or alkylsulphonyl having in each case 1 to 8 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 8 carbon atoms in the individual alkyl moieties;

respectively doubly attached alkylene or dioxyalkylene having in each case 1 to 6 carbon atoms, each of which is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms, $R^3$ represents hydrogen or alkyl having 1 to 4 carbon atoms, $R^4$ represents aryl, cycloalkyl or cycloalkenyl having 3 to 8 carbon atoms, or heterocyclyl having 3 to 12 ring members, each of which is optionally mono- or polysubstituted by identical or different substituents, the substituents being selected from the group consisting of:

halogen, cyano, nitro, amino, hydroxyl, formyl, carboxyl, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;

respectively doubly attached alkylene or dioxyalkylene having in each case 1 to 6 carbon atoms, each of which is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of:

halogen, cyano and/or straight-chain or branched alkyl having 1 to 4 carbon atoms;

and/or straight-chain or branched halogenoalkyl having 1 to 4 carbon atoms and 1 to 9 identical or different halogen atoms;

and/or straight-chain or branched alkoxy or alkylthio having 1 to 4 carbon atoms;

and/or straight-chain or branched halogenoalkoxy or halogenoalkylthio having 1 to 4 carbon atoms and 1 to 9 identical or different halogen atoms;

and/or respectively doubly attached alkylene or dioxyalkylene having in each case 1 to 6 carbon atoms, each of which is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms.

3. Compounds of the formula (I) according to claim 1, in which

A represents a single bond or represents methylene, 1,1-ethylene, 1,2-ethylene 1,1-, 1,2-, 1,3- or 2,2-propylene, 1,1-, 1,2-, 1,3-, 1,4-, 2,2- or 2,3-butylene or 1,1-, 1,2- or 1,3-(2-methylpropylene), each of which is optionally mono- or polysubstituted by identical or different substituents from the group consisting of fluorine, chlorine, cyano and methoxy, Q represents oxygen or sulphur, $R^1$ represents respectively optionally mono- to trisubstituted cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the substituents being selected from the group consisting of:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents selected from the group consisting of fluorine, chlorine, methyl, trifluoromethyl, ethyl, n- and i-propyl;

cyclopropyl, cyclobutyl, cyclopentyl or cyclohexyl;

phenyl, benzyl, phenoxy, benzyloxy, each of which is optionally substituted by the abovementioned substituents;

$R^2$ represents methyl, ethyl, n- or i-propyl, n-, i-, s- or t-butyl or propargyl or allyl, or represents respectively optionally mono- to trisubstituted cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the substituents being selected from the group consisting of:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl;

or represents benzyl which is substituted the abovementioned substituents, $R^3$ represents hydrogen or represents methyl or ethyl, $R^4$ represents optionally mono- to trisubstituted cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the substituents being selected from the group consisting of:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl, cyclopropyl, cyclobutyl, cyclopentyl or cyclohexyl.

4. Compounds of the formula (I) according to claim 1, in which

A represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally mono- or polysubstituted by identical or different substituents from the group consisting of fluorine, chlorine, cyano and methoxy, Q represents oxygen or sulphur, $R^1$ represents respectively optionally mono- to hexasubstituted cyclobutyl, cyclopentyl or cyclohexyl, the substituents being those listed below;

represents respectively optionally mono- to trisubstituted phenyl, naphthyl, furyl, benzofuranyl, thienyl, benzothienyl, pyridyl, quinolyl, tetrahydrofuryl or perhydropyranyl, the substituents being selected from the group consisting of:

fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl; cyclopropyl, cyclopentyl, cyclohexyl; phenyl, phenoxy, benzyloxy, each of which is optionally substituted by the abovementioned substituents;

$R^2$ represents methyl, ethyl, n-, i-propyl, n-, i-, s- or t-butyl, allyl, or represents respectively optionally mono- to hexasubstituted cyclobutyl, cyclopentyl or cyclohexyl, the substituents being those listed below;

or represents respectively optionally mono- to trisubstituted phenyl, naphthyl, furyl, benzofuranyl, thienyl, benzothienyl, pyridyl, quinolyl, tetrahydrofuryl or perhydropyranyl, the substituents being selected from the group consisting of:

fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- or i-propyl, or represents benzyl which is substituted by the abovementioned substituents, $R^3$ represents hydrogen or represents methyl, $R^4$ represents respectively optionally mono- to hexasubstituted cyclopropyl, cyclobutyl, cyclopentyl or cyclohexyl, the substituents being those listed below;

represents respectively optionally mono- to trisubstituted phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the substituents being selected from the group consisting of:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl;

cyclopropyl, cyclobutyl, cyclopentyl or cyclohexyl.

5. Compounds of the formula (I) according to claim 1, in which

A represents a single bond or represents methylene, 1,1-ethylene, 1,2-ethylene, 1,1-propylene, 1,2-propylene, 1,3-propylene or 2,2-propylene, Q represents oxygen, $R^1$ represents phenyl, thienyl or furanyl, each of which is optionally mono- or disubstituted by bromine, chlorine, fluorine, nitro, methylsulphonyl, phenyl, phenyloxy, benzyloxy, cyclopropyl, cyclohexyl, methyl, ethyl, n- or i-propyl, n-, i-, s- or t-butyl, n-pentyl, n-hexyl, n-heptyl, methoxy, ethoxy, trifluoromethyl, trifluoromethoxy and/or methylthio, or represents phenyl which is substituted by 3,4-methylene- and ethylenedioxo, propane-1,3-diyl and butane-1,4-diyl, each of which is optionally substituted by fluorine, or represents naphthyl, benzofuranyl or benzothienyl, $R^2$ represents methyl or ethyl, represents n- or i-propyl, represents n-, i-, s- or t-butyl, allyl, cyclopentyl, cyclohexyl or represents optionally chlorine-, methyl- or methoxy-substituted phenyl or benzyl, $R^3$ represents hydrogen or methyl, $R^4$ represents cyclohexyl or optionally mono- to trisubstituted phenyl, thienyl, furyl, benzofuryl, benzothienyl, pyridyl, pyrimidinyl, naphthyl, quinolyl, the substituents being selected from the group consisting of:

fluorine, chlorine, bromine, cyano, nitro, amino, hydroxyl, formyl, carboxy, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl, respectively doubly attached trimethylene (propane-1,3-diyl), tetramethylene (butane-1,4-diyl), methylenedioxy or ethylenedioxy, each of which is optionally mono- or polysubstituted by identical or different substituents from the group consisting of fluorine, chlorine, methyl, trifluoromethyl, ethyl, n- and i-propyl.

6. Process for preparing pesticides, characterized in that compounds of the formula (I) according to claim 1 are mixed with extenders and/or surfactants.

7. Process for preparing compounds of the formula (I) according to claim 1, comprising reacting carboxylic acid derivatives of the formula (II)

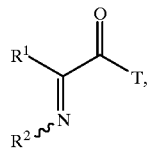
(II)

in which

R$^1$, R$^2$ and Q are each as defined in claim 1 and

T represents hydroxyl, halogen or alkoxy, are reacted with an amine of the general formula (III),

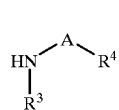
(III)

in which

R$^3$, R$^4$ and A are each as defined in claim 1, or with a hydrogen halide thereof if appropriate in the presence of an acid acceptor, if appropriate in the presence of a condensing agent, if appropriate in the presence of a catalyst and if appropriate in the presence of a diluent.

8. A pesticidal composition comprising a pesticidally effective amount of a compound of the formula (I) according to claim 1 or a mixture of compounds of the formula (I) and one or more extenders and/or one or more surfactants.

9. A method for controlling pests comprising applying to pests and/or their habitat a pesticidally effective amount of a compound of the formula (I) according to claim 1 or of a mixture of compounds of the formula (I).

10. A process for preparing a pesticidal composition according to claim 8 comprising mixing at least one compound of the formula (I) according to claim 1 and one or more extenders and/or one or more surfactants.

* * * * *